(12) United States Patent
Ratts et al.

(10) Patent No.: US 9,360,463 B1
(45) Date of Patent: Jun. 7, 2016

(54) METHOD AND SYSTEM FOR TESTING A CONDITION OF A CATALYST

(71) Applicant: Caterpillar Inc., Peoria, IL (US)

(72) Inventors: Joshua Ratts, East Peoria, IL (US); Wilce Damion Williams, Peoria, IL (US); Robert D. Clayton, Jr., Peoria, IL (US)

(73) Assignee: Caterpillar Inc., Peoria, IL (US)

( * ) Notice: Subject to any disclaimer, the term of this patent is extended or adjusted under 35 U.S.C. 154(b) by 0 days.

(21) Appl. No.: 14/633,510

(22) Filed: Feb. 27, 2015

(51) Int. Cl.
*B01J 19/00* (2006.01)
*G01N 31/10* (2006.01)
*G01N 31/00* (2006.01)

(52) U.S. Cl.
CPC .............. *G01N 31/10* (2013.01); *B01J 19/00* (2013.01); *B01J 19/0046* (2013.01); *G01N 31/00* (2013.01)

(58) Field of Classification Search
CPC ................ B01J 19/0046; B01J 19/00; B01J 2219/00585; B01J 2219/00583; B01J 2219/00745; B01J 2219/00718; B01J 19/00; G01N 31/10; G01N 31/00
USPC ........................................................ 436/37
See application file for complete search history.

(56) References Cited

U.S. PATENT DOCUMENTS

| | | | |
|---|---|---|---|
| 3,667,914 A | 6/1972 | Penquite et al. | |
| 4,071,324 A | 1/1978 | Reid | |
| 4,691,562 A | 9/1987 | Abthoff et al. | |
| 7,435,598 B2 | 10/2008 | Vaughn et al. | |
| 7,575,931 B2 * | 8/2009 | Steichen | B01D 53/346 436/106 |

* cited by examiner

*Primary Examiner* — Christine T Mui

(57) ABSTRACT

A method for testing a condition of a catalyst is provided. The method includes providing a gas source in communication with the catalyst. The method also includes passing compressed gas from the gas source over the catalyst at normal operating temperature. The method further includes invoking a reaction with the catalyst based on the passage of the compressed gas. The method includes measuring a performance of the catalyst based on the reaction.

9 Claims, 4 Drawing Sheets

METHOD AND SYSTEM FOR TESTING A CONDITION OF A CATALYST

TECHNICAL FIELD

The present disclosure relates to a diagnostic system and an operation thereof, and more particularly to a method and system for testing a condition of a catalyst.

BACKGROUND

An aftertreatment system is associated with an engine system. The aftertreatment system is configured to treat and reduce oxides of nitrogen (NOx) present in an exhaust gas flow, prior to the exhaust gas flow exiting into the atmosphere. In order to reduce NOx, the aftertreatment system may include a reductant delivery module, a reductant injector, and a Selective Catalytic Reduction (SCR) module.

The aftertreatment system includes oxidation catalysts, such as a Diesel Oxidation Catalyst (DOC) unit associated therewith. For example, the DOC unit may be used to create a desired ratio of Nitric Oxide (NO) to Nitrogen Dioxide ($NO_2$) in the engine's exhaust gas flow that enhances $NO_X$ reduction within the SCR module provided downstream of the DOC unit. In another example, the DOC unit can be used to increase an overall amount of $NO_2$ in the exhaust gas flow passing through a Diesel Particulate Filter (DPF) unit to lower a combustion temperature of particulate matter trapped in the DPF unit, and thereby enhance passive regeneration of the DPF unit.

Over a period of time, active catalytic materials present on the oxidation catalyst of the DOC unit, which may include precious materials such as platinum, rhodium, and/or palladium, may agglomerate and become less active, thereby affecting a performance metrics of the oxidation catalyst. Further, an accumulation of materials, such as particles of lubricating oil, may also affect the performance of the oxidation catalysts. A reduction in performance metrics of the oxidation catalyst may affect an overall operation of the aftertreatment system, which is not desirable. Therefore, it is necessary to test the performance of the oxidation catalysts at predetermined intervals in order to make sure that the oxidation catalyst is performing as intended.

Known solutions of testing the catalyst include heaters that are configured to heat a gas which is then flown over the catalysts. In another example, as described in U.S. Pat. No. 3,667,914, the catalyst is heated in an electric furnace. Further, a predetermined exhaust gas mixture or mixtures is passed through the catalyst at a desired test temperature. A pressure drop measurement is then made across the catalyst in order to determine a degradation of the catalyst bed. However, these solutions are expensive and time consuming Further, in some situations, the heating of the catalyst or passage of the heated gas may alter one or more properties of the catalyst and lead to a degradation thereof.

SUMMARY OF THE DISCLOSURE

In one aspect of the present disclosure, a method for testing a condition of a catalyst is provided. The method includes providing a gas source in communication with the catalyst. The method also includes passing compressed gas from the gas source over the catalyst at normal operating temperature. The method further includes invoking a reaction with the catalyst based on the passage of the compressed gas. The method includes measuring a performance of the catalyst based on the reaction.

In another aspect of the present disclosure, a diagnostic system for testing a condition of a catalyst is provided. The diagnostic system includes a gas source. The diagnostic system also includes a flow control device operatively coupled to the gas source and the catalyst. The flow control device is configured to pass compressed gas from the gas source over the catalyst at normal operating temperature. The diagnostic system further includes a measuring device coupled to the catalyst. The measuring device is configured to measure a performance of the catalyst based on a reaction invoked with the catalyst on the passage of the compressed gas thereover.

Other features and aspects of this disclosure will be apparent from the following description and the accompanying drawings.

DETAILED DESCRIPTION

Figure 1:
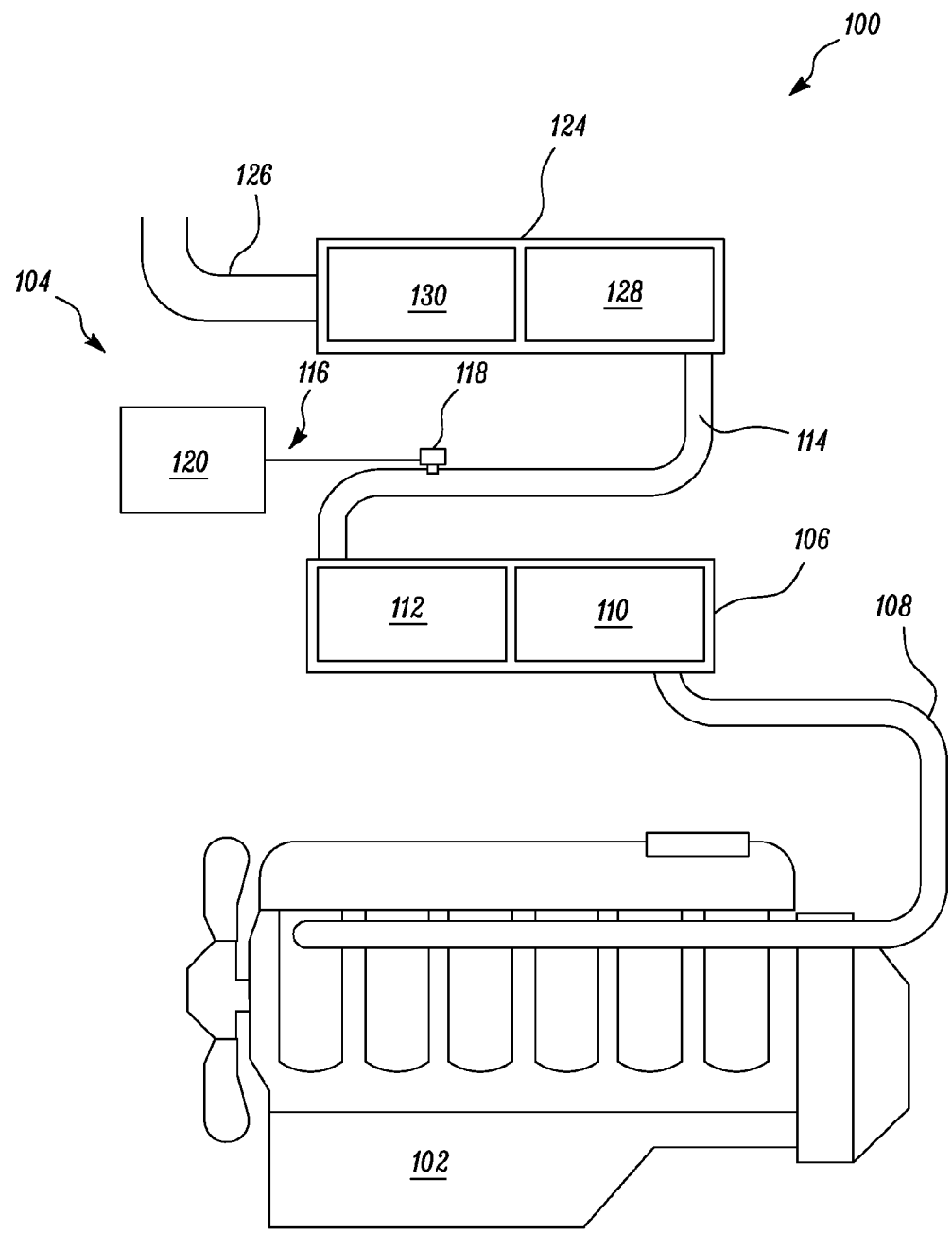
FIG. 1 is a schematic view of an exemplary engine system, according to one embodiment of the present disclosure.

Wherever possible, the same reference numbers will be used throughout the drawings to refer to the same or the like parts. Referring to FIG. 1, a schematic diagram of an exemplary engine system 100 is illustrated, according to one embodiment of the present disclosure. The engine system 100 includes an engine 102, which may be an internal combustion engine, such as, a reciprocating piston engine or a gas turbine engine. The engine 102 is a spark ignition engine or a compression ignition engine, such as, a diesel engine, a homogeneous charge compression ignition engine, or a reactivity controlled compression ignition engine, or other compression ignition engines known in the art. The engine 102 may be fueled by gasoline, diesel fuel, biodiesel, dimethyl ether, alcohol, natural gas, propane, hydrogen, combinations thereof, or any other combustion fuel known in the art.

The engine 102 may include other components (not shown), such as, a fuel system, an intake system, a drivetrain including a transmission system, and so on. The engine 102 may be used to provide power to any machine including, but not limited to, an on-highway truck, an off-highway truck, an earth moving machine, an electric generator, and so on. Accordingly, the engine system 100 may be associated with an industry including, but not limited to, transportation, construction, agriculture, forestry, power generation, and material handling.

Referring to FIG. 1, the engine system 100 includes an aftertreatment system 104 fluidly connected to an exhaust manifold of the engine 102. The aftertreatment system 104 is configured to treat an exhaust gas flow exiting the exhaust manifold of the engine 102. The exhaust gas flow contains emission compounds that may include oxides of nitrogen (NOx), unburned hydrocarbons, particulate matter, and/or other combustion products known in the art. The aftertreatment system 104 may be configured to trap or convert NOx, unburned hydrocarbons, particulate matter, combinations thereof, or other combustion products present in the exhaust gas flow, before exiting the engine system 100.

In the illustrated embodiment, the aftertreatment system 104 includes a first module 106 that is fluidly connected to an exhaust conduit 108 of the engine 102. During engine operation, the first module 106 is arranged to internally receive engine exhaust gas from the exhaust conduit 108. The first module 106 may contain various exhaust gas treatment devices, such as, a Diesel Oxidation Catalyst (DOC) unit 110 and a Diesel Particulate Filter (DPF) unit 112, but other devices may be used.

In the illustrated embodiment, the exhaust gas flow provided to the first module 106 by the engine 102 may first pass through the DOC unit 110 and then through the DPF unit 112 before entering a mixing tube 114. The aftertreatment system 104 includes a reductant supply system 116. A reductant is injected into the mixing tube 114 by a reductant injector 118. The reductant may be a fluid, such as, Diesel Exhaust Fluid (DEF). The reductant may include urea, ammonia, or other reducing agent known in the art.

The reductant supply system 116 includes a reductant tank 120. The reductant is contained within the reductant tank 120. Parameters related to the reductant tank 120 such as size, shape, location, and material used may vary according to system design and requirements. Further, the reductant injector 118 may be communicably coupled to a controller (not shown). Based on control signals received from the controller, the reductant from the reductant tank 120 is provided to the reductant injector 118 by a pump assembly (not shown).

As the reductant is injected into the mixing tube 114, the reductant mixes with the exhaust gas flow passing therethrough, and is carried to a second module 124. Further, the mixing tube 114 is configured to fluidly interconnect the first module 106 with the second module 124, such that, the exhaust gas flow from the engine 102 may pass through the first and second modules 106, 124 in series before being released at a stack 126 connected downstream of the second module 124. The second module 124 encloses a Selective Catalytic Reduction (SCR) module 128 and an Ammonia Oxidation Catalyst (AMOX) 130. The SCR module 128 operates to treat exhaust gases exiting the engine 102 in the presence of ammonia, which is provided after degradation of the reductant injected into the exhaust gases in the mixing tube 114. The AMOX 130 is used to convert any ammonia slip from the downstream flow of the SCR module 128 before exiting the stack 126. The aftertreatment system 104 disclosed herein is provided as a non-limiting example. It will be appreciated that the aftertreatment system 104 may be disposed in various arrangements and/or combinations relative to the exhaust manifold. These and other variations in aftertreatment system design are possible without deviating from the scope of the disclosure.

It should be noted that the DOC unit 110, the SCR module 128, and/or the AMOX 130 may include catalysts associated therewith. The particulate matter present in the exhaust gas flow may stick to and buildup on the catalysts over a period of time, and if left unchecked, the particulate matter buildup could be significant enough to restrict or in some cases block the flow of the exhaust gases therethrough. A restriction in the outflow of exhaust gases may increase a back pressure in the engine 102. The backpressure in the engine 102 may reduce the engine's ability to draw in fresh air, resulting in decreased performance, increased exhaust temperatures, and poor fuel consumption. Further, an agglomeration or centering of precious metals, such as palladium, platinum, or rhodium that are provided on a surface of the catalyst may also affect a performance of the catalysts. The catalysts present in the DOC unit 110, the SCR module 128, and/or the AMOX 130 of the engine system 100 may therefore require periodic evaluation in order to test a condition and/or performance of the catalyst.

Figure 2:
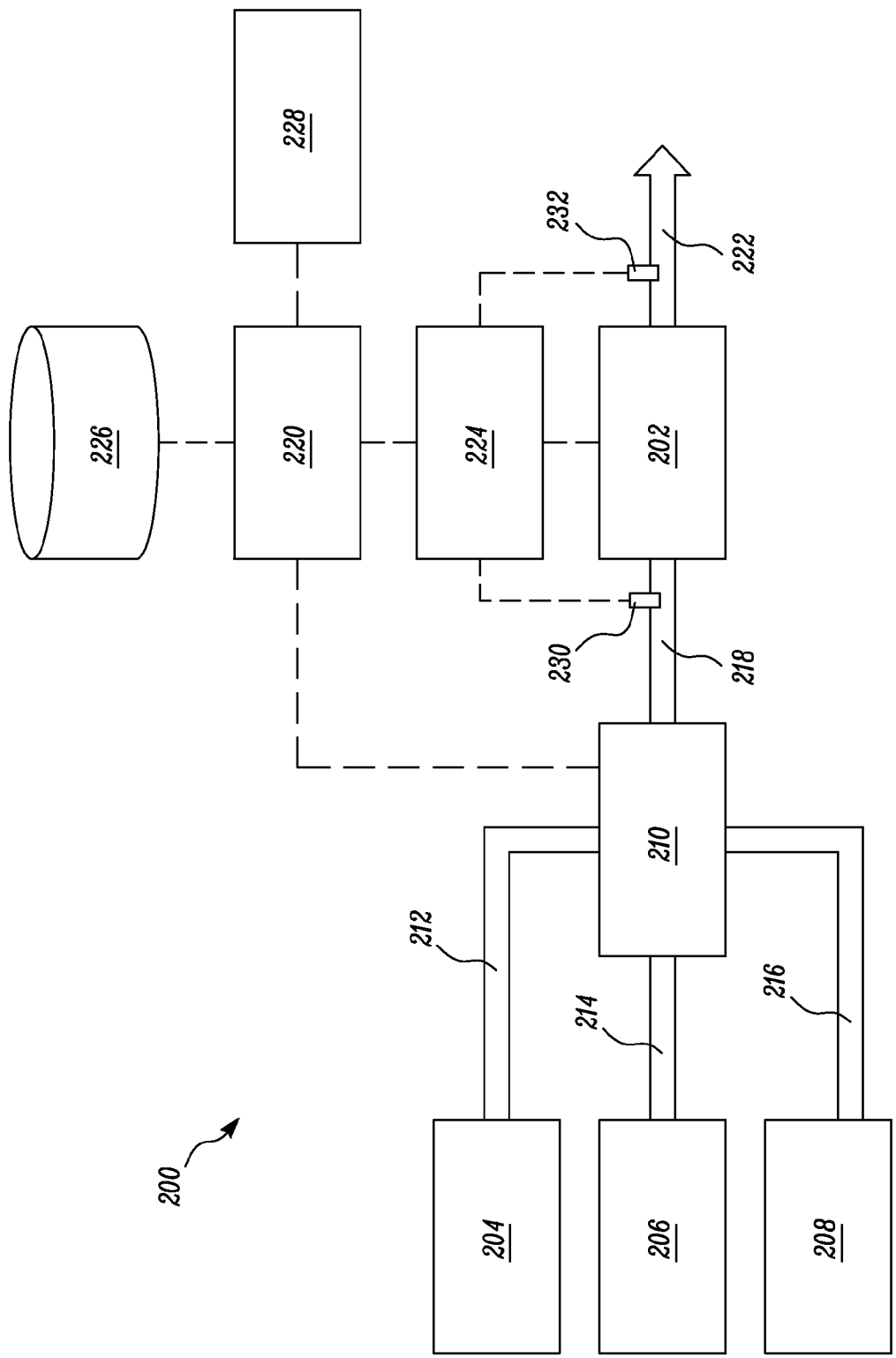
FIG. 2 is a block diagram of a diagnostic system, according to one embodiment of the present disclosure.

FIG. 2 is a block diagram of a diagnostic system 200 associated with the engine system 100. In the illustrated embodiment, the diagnostic system 200 is configured to test a condition of the catalyst 202 of the DOC unit 110. However, it should be understood that the application of the present disclosure may be extended to be used for testing of any catalyst, and more particularly, a catalyst containing precious metals. Further, the catalysts may be associated with any of an SCR module, soot oxidation catalytic units, AMOX, and the like.

The diagnostic system 200 includes a gas source which stores compressed gases therein. In the illustrated embodiment, the diagnostic system 200 includes a first gas source 204 and a second gas source 206. The first gas source 204 is configured to store compressed air therein. For example, the first gas source 204 may store house air which is in a compressed form. Further, the second gas source 206 is configured to store compressed hydrogen ($H_2$) gas therein. Further, due to flammability concerns associated with $H_2$ gas, the second gas source 206 may store a mixture of $H_2$ gas and nitrogen ($N_2$) gas. In one example, the second gas source 206 may store 4% to 5% or less of $H_2$ gas therein, while a remaining percentage of the gases may include $N_2$ gas.

In one embodiment, the diagnostic system 200 may additionally or optionally include a third gas source 208. The third gas source 208 is configured to store a mixture of nitric oxide (NO) gas and $N_2$ gas therein. In one example, the third gas source 208 may store up to 1% or less of NO gas therein, while a remaining percentage of the gases may include $N_2$ gas. The first, second, and third gas sources 204, 206, 208 may embody any cylinder or reservoir capable of storing gases in a compressed form. Alternatively, the diagnostic system 200 may include a single gas source with partitions, such that each partition of the single gas source is isolated from each other, and is configured to store different gases therein.

The first, second, and third gas sources 204, 206, 208 are provided in fluid communication with the catalyst 202 via a flow control device 210. The flow control device 210 is operatively coupled to the first, second, and third gas sources 204, 206, 208 and the catalyst 202. The flow control device 210 is configured to receive and meter the gases from the first, second, and third gas sources 204, 206, 208, via conduits 212, 214, 216 respectively. Further, the flow control device 210 is configured to mix the gases received from the first, second, and third gas sources 204, 206, 208 and pass a mixture of the compressed gases, hereinafter referred to as the compressed gas flow, over the catalyst 202 at normal operating temperature, via conduit 218.

In one example, the flow control device 210 may be communicably coupled to a control module 220 and may receive control signals therefrom. The signals may include, for example, signals to actuate or de-actuate the flow control device 210 or an amount of a particular gas that needs to be maintained in the compressed gas flow. The flow control device 210 may include any flow metering and control device that selectively allows or restricts a metered flow of gases therethrough. In one example, the flow control device 210 may include a rotameter. Alternatively, a mass flow controller or a needle valve may also be used, without limiting the scope of the present disclosure.

When the compressed gas flow passes over the catalyst 202 at normal temperature, a reaction is invoked with the catalyst 202. For example, when the compressed gas flow includes a mixture of air and $H_2$ gas received from the first and second gas source 204, 206 respectively, an oxidation reaction may be invoked with the catalyst 202. More specifically, the $H_2$ gas may react with oxygen ($O_2$) gas present in the compressed air, to form a product. In this example, the product formed is water ($H_2O$). The reaction occurring at the catalyst 202 is as given below.

$$2H_2 + O_2 \rightarrow 2H_2O \qquad \text{Equation (i)}$$

However, it should be noted that due to the presence of precious metals in the catalysts 202, the reaction in Equation (i) occurring at the catalyst 202 is a fast reaction. Hence, it may be difficult to analyze a change in the catalyst's activity. Thus, in order to monitor the reaction occurring with the catalyst 202, the rate of the reaction may have to be slowed down. Therefore, in such situations, the NO gas from the third gas source 208 is metered and mixed with the $O_2$ in the air and $H_2$ gas, to slow down the reaction. In this case, the compressed gas flow includes a mixture of $O_2$ gas, $H_2$ gas, and NO gas. Further, in this example, the product so formed includes $H_2O$, nitrous oxide ($N_2O$) gas, ammonia ($NH_3$) gas, and $N_2$ gas. The reactions occurring at the catalyst 202 in addition to equation (i) are as given below:

$$H_2 + 2NO \rightarrow N_2O + H_2O$$

$$(5/2)H_2 + NO \rightarrow NH_3 + H_2O$$

$$2H_2 + 2NO \rightarrow N_2 + 2H_2O \qquad \text{Equation (ii)}$$

Based on the gases present in the compressed gas flow passing over the catalyst 202, any one of the reactions given above may be invoked at the catalyst 202. As described above, on flowing over the catalyst 202, the compressed gas flow undergoes changes in its composition which converts the compressed gas flow into a residual gas flow. The residual gas flow exiting the catalyst 202 is vented to atmosphere, through a conduit 222. The conduits 212, 214, 216, 218, 222 may include any pipe, tube, duct, or channel capable of conveying fluids therethrough, without limiting the scope of the present disclosure. In one example, the conduits 212, 214, 216, 218, 222 may embody flexible pipes.

Further, it should be noted that the reaction given above are exothermic reactions. The heat so generated may raise a temperature of the catalyst 202 and also the residual gas flow exiting the catalyst 202. As shown in the accompanying figures, the diagnostic system 200 includes a measuring device 224. The measuring device 224 is operatively coupled to the catalyst 202. The measuring device 224 is configured to measure the performance of the catalyst 202 based on the reaction that is invoked with the catalyst 202, on the passage of the compressed gas flow thereover.

In one embodiment of the present disclosure, the measuring device 224 is configured to measure a performance of the catalyst 202, and more particularly the measuring device 224 is configured to measure a parameter associated with the products of the invoked reaction. In this situation, the measuring device 224 receives the residual gas flow from the catalyst 202, and after analyzing the parameter associated with the products, the residual gas flow is vented to the atmosphere. For example, the measuring device 224 may measure an amount of the products of the invoked reaction. In another example, the parameter being measured by the measuring device 224 may include a thermal conductivity of the residual gas flow and more particularly, the change in the thermal conductivity when $H_2O$ is produced. In this example, wherein the measuring device 224 is configured to measure the thermal conductivity of the residual gas flow, the measuring device 224 may embody any one of a thermal conductivity detector, infrared based analyzer, mass spectrometer, or any other analytical device capable of measuring a change in the properties of the residual gas flow or a change in the respective amount of each reactant or product.

In another embodiment of the present disclosure, the measuring device 224 may be configured to measure a rise in temperature of the catalyst 202, the temperature difference between the compressed gas flow and the residual gas flow, or the temperature of the products of the invoked reaction. In such an example, the measuring device 224 may include temperature measuring devices associated therewith. For example, when the measuring device 224 is configured to measure the rise in temperature of the compressed gases flowing over the catalyst 202, the measuring device 224 may include a pair of temperature measuring devices. More particularly, a first temperature measuring device 230 may be mounted at an upstream side of the catalyst 202 with respect to the compressed gas flow. The first temperature measuring device 230 is configured to measure a current temperature of the compressed gas flow prior to the reaction.

Further, a second temperature measuring device 232 is associated with the measuring device 224. The second temperature measuring device 232 is configured to measure a current temperature of the residual gas flow, and is mounted downstream of the catalyst 202 with respect to the compressed gas flow. A difference between the temperatures measured by the first and second temperature measuring devices 230, 232 is a measure of the temperature rise in the compressed gas flow after passing over the catalyst 202, on account of the invoked reaction. In one example, a temperature measuring device (not shown) may be associated with the measuring device 224, wherein the temperature measuring device may be configured to measure the temperature of the residual gas flow.

Alternatively, the measuring device 224 may measure a temperature of the catalyst 202 before and after the reaction. In such an example, the measuring device 224 may include a single temperature measuring device (not shown) associated with the catalyst 202. The temperature measuring device is configured to determine a current temperature of the catalyst 202 prior to the reaction. Further, the temperature measuring device is also configured to measure an increase in a temperature of the catalyst 202 from the current temperature, after the reaction. Accordingly, multiple temperature measuring devices may be positioned at different locations down a length of the catalyst 202.

The temperature measuring devices referred to herein may include any known temperature measuring devices capable of measuring temperature of the compressed gas flow, the residual gas flow, and/or the catalyst 202. The temperature measuring devices may include any contact type or contactless type temperature measuring device. In one example, the temperature measuring device may include a thermocouple. Alternatively, the temperature measuring device may embody a thermistor, resistance temperature detector, pyrometer, infrared temperature measuring device, thermometers, and so on.

The measuring device 224 is communicably coupled to the control module 220. The control module 220 may be configured to receive a signal indicative of the parameters associated with the products of the reaction, the compressed gas flow, the residual gas flow, the catalyst 202, or a combination thereof. Further, a database 226 may be communicably coupled to the control module 220 in a wired or wireless manner. In one example, the database 226 may store respective predetermined metrics corresponding to the products of the reaction, the compressed gas flow, the residual gas flow, the catalyst 202, or a combination thereof. The predetermined metrics are pre-stored values indicative of acceptable performance thresholds for the corresponding parameters of the catalyst 202.

Based on the signals received from the measuring device 224, the control module 220 is configured to retrieve the respective predetermined metric from the database 226. Further, the control module 220 may compare the signals received from the measuring device 224 with the respective predetermined metric retrieved from the database 226. Based on the comparison, the control module 220 is configured to determine a life of the catalyst 202. The determined life of the catalyst 202 may be indicative of whether the catalyst 202 is suitable for use or re-use, as the case may be, or if some corrective actions need to be performed on the catalyst 202 in order to improve the performance thereof. The working of the diagnostic system 200 to determine the life of the catalyst 202 will be explained in detail in connection with FIG. 3.

An output module 228 is communicably coupled to the control module 220 in a wired or wireless manner. The output module 228 is configured to provide a notification of the determined life of the catalyst 202 to a personnel performing the testing of the catalysts 202. The output module 228 may be mounted at a location such that the output module 228 may be viewable to the personnel. The output module 228 may also be present at a location remote to a location where the testing of the catalyst 202 is being performed.

The output module 228 may embody a visual output or an audio output. In one example, wherein the output module 228 is embodied as a visual output, the output module 228 may include any one of a digital display device, an LCD device, an LED device, a CRT monitor, a touchscreen device, or any other display device known in the art. In one example, the output module 228 may notify the personnel regarding the determined life of the catalysts 202 through a text message.

Alternatively, the output module 228 may include an indicator light for example an LED light or an LCD light. For example, if the determined life of the catalyst 202 is such that the catalyst 202 is capable of use, the indicator light glows of a green color. In another example, if the determined life of the catalyst 202 is such that the catalyst 202 is incapable of use, the indicator light glows of a red color. In a situation wherein the output module 228 is embodied as the audio output, an audio clip may be heard, thereby alerting the personnel of the determined life of the catalyst 202. It should be noted that the output module 228 may include any other means other than those listed above.

Figure 3:
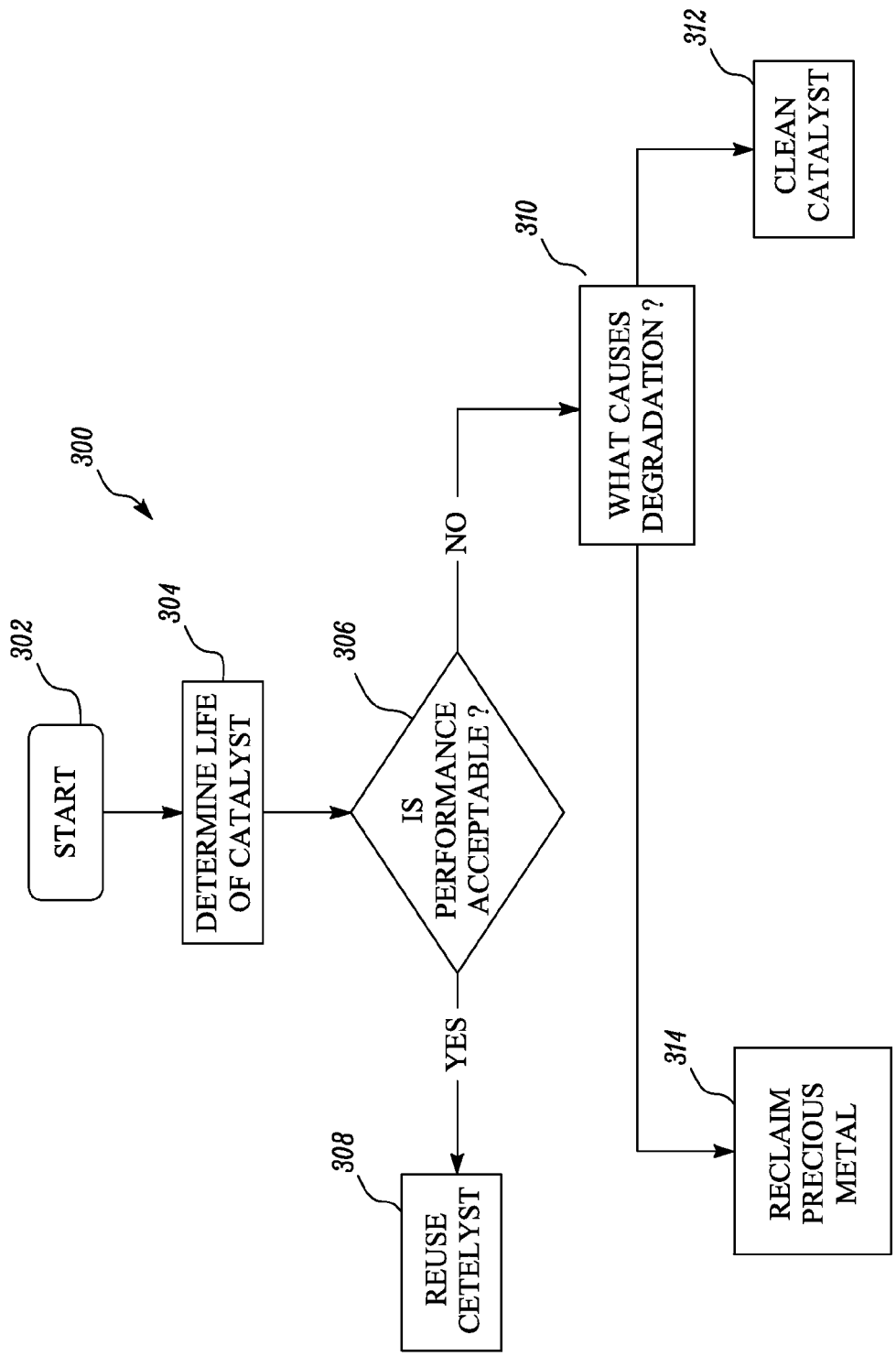
FIG. 3 is a flowchart for a method of deciding an action to be performed based on a determined life of a catalyst.

FIG. 3 is a process 300 that may be stored in the control module 220 in order to identify an action to be performed on the catalyst 202, based on the determined life of the catalyst 202. Alternatively, the process 300 may also be stored in an electronic control module (ECM) present on-board the machine, and may be retrieved by the control module 220 therefrom.

The process 300 (or algorithm) begins at step 302 in which the method implemented by the control module 220 starts or begins operation. At step 304, the process 300 is configured to determine the life of the catalyst 202.

As explained earlier, based on the comparison between the signals received from the measuring device 224 and the corresponding predetermined metrics retrieved from the database 226, the control module 220 is configured to determine the life of the catalyst 202. As step 306, based on the determined life of the catalyst 202, the control module 220 evaluates whether the performance of the catalyst 202 is acceptable for further use.

If the determined life of the catalyst 202 is indicative that the catalyst 202 has an acceptable performance, the process 300 may move on to step 308, and indicating to the personnel that the catalyst 202 may be re-used without performing any additional actions or maintenance procedures thereon. The indication may be sent to the personnel through the output module 228 associated with the diagnostic system 200. In case the performance of the catalyst 202 is evaluated as not acceptable, the process 300 may move onto step 310. At step 310, the control module 220 is configured to determine the factors that may have caused a degradation in the performance of the catalysts 202. In one example, if the degradation in the performance of the catalyst 202 is on account of a chemical reaction, such as accumulation of oil or other foreign particles on a surface of the catalyst 202, the process 300 may move onto step 312. At step 312, the control module 220 may indicate, through the output module 228, that the catalyst 202 may have to be serviced in order to improve the performance. Based on the indication provided, the catalyst 202 may be cleaned or treated, for example, the catalyst 202 may be acid washed.

Further, if the degradation in the performance of the catalyst 202 is on account of a hydrothermal reaction, the process 300 may move onto step 314. In one example, the hydrothermal reaction may be caused due to an agglomeration or centering of the precious metals on the surface of the catalyst 202. Therefore, at step 314, the control module 220 may indicate, through the output module 228, that the precious metals in the catalyst 202 need to be reclaimed.

The location of the database 226 may vary based on the application. The predetermined thresholds stored within the database 226 may be retrieved from any external source(s) and/or updated on a real time basis. The database 226 may be any conventional or non-conventional database known in the art. Moreover, the database 226 may be capable of storing and/or modifying pre-stored data as per operational and design needs.

The control module 220 may embody a single microprocessor or multiple microprocessors for receiving signals from components of the engine system 100. Numerous commercially available microprocessors may be configured to perform the functions of the control module 220. It should be appreciated that the control module 220 may embody a machine microprocessor capable of controlling numerous machine functions. A person of ordinary skill in the art will appreciate that the control module 220 may additionally include other components and may also perform other functions not described herein.

INDUSTRIAL APPLICABILITY

The diagnostic system 200 of the present disclosure does not alter or modify the composition of the catalyst 202, as the procedure conducted by the system 200 takes place at normal operating temperature and does not make use of heat. Hence, the catalyst 202 is not in any way degraded or rendered useless after the testing process. The diagnostic system 200 is easy to operate, and involves the use of fewer components. Also, the testing of the catalyst 202 using the diagnostic system 200 is cost effective and gives close to accurate results. Further, the testing of the catalyst 202 may be done in a relatively short period of time.

Figure 4:
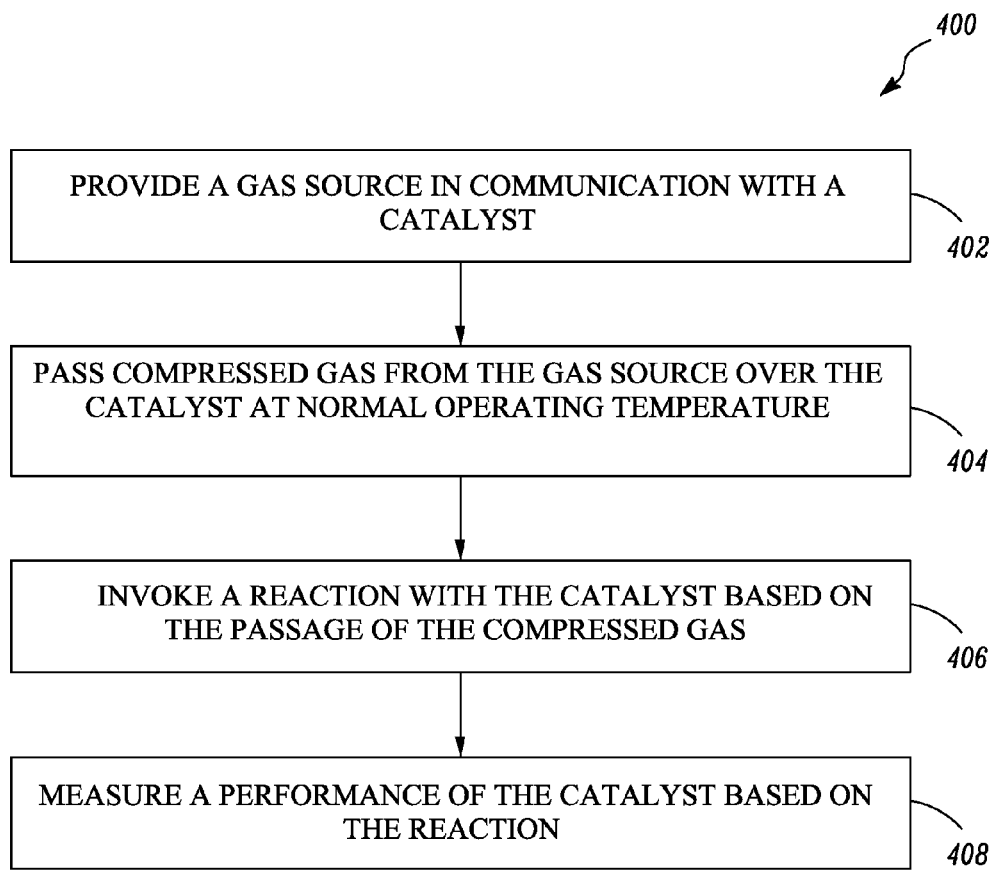
FIG. 4 is a flowchart for a method of testing a condition of the catalyst.

FIG. 4 is a flowchart for a method 400 of testing the condition of the catalyst 202. At step 402, the first, second, and third gas sources 204, 206, 208 are provided in communication with the catalyst 202. At step 404, the compressed gas flow received from the first, second, and third gas sources 204, 206, 208 and the flow control device 210 is passed over the catalyst 202 at normal operating temperature. The compressed gas flow includes the mixture of compressed air and compressed $H_2$ gas. In one embodiment, the compressed gas flow may also include compressed NO gas.

At step 406, the reaction is invoked with the catalyst 202 based on the passage of the compressed gas flow thereover. At step 408, the performance of the catalyst 202 is measured based on the reaction. In one example, the measuring device 224 is configured to measure the thermal conductivity of the residual gas flow. In another example, the measuring device 224 determines the current temperature of the catalyst 202 prior to the reaction. Further, the measuring device 224 also measures the increase in the temperature of the catalyst 202 from the current temperature of the catalyst 202. In yet another example, the measuring device 224 is configured to measure the temperature of the compressed gas flow prior to passage over the catalyst 202 and also the temperature of the residual gas flow. In some embodiments, the measuring device 224 measures the temperature of the residual gas flow.

Further, the control module 220 of the diagnostic system 200 is configured to compare the measured performance of the catalyst 202 with the predetermined metric. Based on the comparison, the control module 220 is configured to determine the life of the catalyst 202. The determined life of the catalyst 202 is notified to the personnel using the output module 228. The control module 220 also gives an indication of which further actions need to be performed on the catalyst 202, if the performance on the catalyst 202 is determined to be acceptable or unacceptable. These actions may include any one of re-using the catalyst 202, cleaning the catalyst 202, or reclaiming precious metals from the catalyst 202.

While aspects of the present disclosure have been particularly shown and described with reference to the embodiments above, it will be understood by those skilled in the art that various additional embodiments may be contemplated by the modification of the disclosed machines, systems and methods without departing from the spirit and scope of what is disclosed. Such embodiments should be understood to fall within the scope of the present disclosure as determined based upon the claims and any equivalents thereof.

What is claimed is:

1. A diagnostic system for testing a condition of a catalyst, the diagnostic system comprising:
   a gas source including a first gas source of compressed air and a second gas source of compressed hydrogen gas;
   a flow control device operatively coupled to the gas source and the catalyst, the flow control device configured to pass compressed gas from the gas source over the catalyst at normal operating temperature; and
   a measuring device coupled to the catalyst, the measuring device configured to measure a performance of the catalyst based on a reaction invoked with the catalyst on passage of the compressed gas over the catalyst.

2. The diagnostic system of claim 1, wherein the second gas source includes a mixture of compressed hydrogen gas and compressed nitrogen gas.

3. The diagnostic system of claim 1, wherein the gas source further includes a third gas source of a mixture of compressed nitric oxide gas and compressed nitrogen gas.

4. The diagnostic system of claim 1, wherein the measuring device is further configured to measure a thermal conductivity of a residual gas flow.

5. The diagnostic system of claim 1, wherein the measuring device is further configured to determine a current temperature of the catalyst prior to the reaction.

6. The diagnostic system of claim 5, wherein the measuring device is further configured to measure an increase in a temperature of the catalyst from the current temperature of the catalyst.

7. The diagnostic system of claim 1, wherein the measuring device is further configured to measure a temperature of a residual gas flow.

8. The diagnostic system of claim 1, wherein the measuring device is further configured to:
   compare the measured performance of the catalyst with a predetermined metric; and
   determine a life of the catalyst based on the comparison.

9. The diagnostic system of claim 8 further comprising an output module coupled to the measuring device, the output module configured to provide a notification of the determined life of the catalyst.

* * * * *